(12) United States Patent
Shin et al.

(10) Patent No.: US 11,543,892 B2
(45) Date of Patent: Jan. 3, 2023

(54) TOUCH PRESSURE INPUT FOR DEVICES

(71) Applicant: GOOGLE LLC, Mountain View, CA (US)

(72) Inventors: Dongeek Shin, Santa Clara, CA (US); Shahram Izadi, Tiburon, CA (US); Shwetak N. Patel, Seattle, WA (US)

(73) Assignee: GOOGLE LLC, Mountain View, CA (US)

( * ) Notice: Subject to any disclaimer, the term of this patent is extended or adjusted under 35 U.S.C. 154(b) by 0 days.

(21) Appl. No.: 17/302,258

(22) Filed: Apr. 28, 2021

(65) Prior Publication Data

US 2022/0350419 A1    Nov. 3, 2022

(51) Int. Cl.
*G06F 3/02*    (2006.01)
*A61B 5/282*    (2021.01)
*A61B 5/332*    (2021.01)
*A61B 5/00*    (2006.01)

(52) U.S. Cl.
CPC ............ *G06F 3/0202* (2013.01); *A61B 5/282* (2021.01); *A61B 5/332* (2021.01); *A61B 5/681* (2013.01); *A61B 5/6898* (2013.01)

(58) Field of Classification Search
CPC ....... G06F 3/0202; A61B 5/282; A61B 5/332; A61B 5/681; A61B 5/6898
See application file for complete search history.

(56) References Cited

U.S. PATENT DOCUMENTS

| 2013/0190638 | A1  | 7/2013  | Chon et al. |
| 2015/0272457 | A1* | 10/2015 | Etemad ............... A61B 5/02438 600/509 |
| 2015/0309582 | A1* | 10/2015 | Gupta ..................... G06F 3/017 345/156 |
| 2018/0232589 | A1* | 8/2018  | Woo ................... G06K 9/00885 |
| 2021/0278947 | A1* | 9/2021  | Choi ................... G06F 3/04842 |

OTHER PUBLICATIONS

Lourenco, et al., "Unveiling the Biometric Potential of Finger-Based ECG Signals", Hindawi Publishing Corporation Computational Intelligence and Neuroscience; vol. 2011, Article ID 720971; Jun. 14, 2011, 8 pages.

* cited by examiner

*Primary Examiner* — Alexander Eisen
*Assistant Examiner* — Kebede T Teshome
(74) *Attorney, Agent, or Firm* — Brake Hughes Bellermann LLP

(57) ABSTRACT

A computing device, such as a wearable device, may include at least two electrodes mounted on a body. The computing device may determine an electrical signal associated with a circuit that includes the at least two electrodes and the user. A pressure applied to at least one electrode of the at least two electrodes may be determined from the electrical signal, and at least one function of the computing device may be implemented, based on the pressure.

18 Claims, 14 Drawing Sheets

1026

1028  1030  1032

| Layer (type) | Output Shape | Param # |
|---|---|---|
| Input_4 (InputLayer) | [(None, 250, 1)] | 0 |
| Convid_6 (ConvID) | (None, 82, 21) | 126 |
| average_poolingid_6 (Average) | (None, 41, 21) | 0 |
| convid_7 (ConvID) | (None, 39, 11) | 704 |
| average_poolingid_7 (Avverage) | (None, 39, 11) | 0 |
| flatten_3 (Flatten) | (None, 209) | 0 |
| dense_9 (Dense) | (None, 32) | 6720 |
| dropout_6 (Dropout) | (None, 32) | 0 |
| dense_10 (Dense) | (None, 2) | 66 |

Total params: 7,616
Trainable params: 7,616
Non-trainable params: 0

1034

FIG. 10C ness and many types of wearable devices, provide a large number and variety of features and functions to users. These features and functions are associated with corresponding types of human interface components, which enable the users to control the computing device in desired manners.

TOUCH PRESSURE INPUT FOR DEVICES

TECHNICAL FIELD

This description relates to device control using touch pressure input.

BACKGROUND

Computing devices, including computers, smartphones, and many types of wearable devices, provide a large number and variety of features and functions to users. These features and functions are associated with corresponding types of human interface components, which enable the users to control the computing device in desired manners.

SUMMARY

According to a general aspect, a computing device may include a processor, a storage medium storing instructions, a body, and at least two electrodes mounted on the body and in contact with a user of the computing device (when using the device properly, i.e., as provided for). The instructions, when executed by the processor, cause the computing device to determine an electrical signal associated with a circuit that includes the at least two electrodes and the user, determine, from the electrical signal, a pressure applied to at least one electrode of the at least two electrodes, and implement at least one function of the computing device, based on the pressure. A computer-implemented method may be executed using the computing device, and a computer program product may be stored on the storage medium to cause the computing device to execute the computer-implemented method.

The details of one or more implementations are set forth in the accompanying drawings and the description below. Other features will be apparent from the description and drawings, and from the claims.

BRIEF DESCRIPTION OF THE DRAWINGS

FIG. 10C is a table illustrating example parameters of the example of FIG. 10B

DETAILED DESCRIPTION

Described systems and techniques enable touch pressure interactions of users with devices, including wearable devices, without requiring a dedicated pressure sensor. For example, a wearable device may be outfitted with at least two electrodes, positioned to enable the user to complete a closed circuit by touching the at least two electrodes. The closed circuit includes the at least two electrodes and the user, e.g., at least a portion of the body of the user. The device, e.g., wearable device, is configured to determine a relative or absolute level of pressure applied to at least one of the at least two electrodes touched by the user when completing the closed circuit. In this way, the device may perform various types of functions in response to the determined pressure, thereby providing the user with convenient and intuitive modes of interaction with the device.

Conventional techniques for implementing pressure-based device control utilize or rely on one or more dedicated pressure sensors, such as capacitive sensors, and/or sensors that attempt to measure a distance moved by a pressed element (e.g., a button, or a portion of a touchscreen). Such pressure sensors may be relatively expensive and/or unreliable (e.g., may produce unreliable measurements, or otherwise prone to malfunction). Moreover, such pressure sensors may be undesirably large, and it may be difficult or impossible to include such pressure sensors on devices with small form factors, such as wearable devices, or in any use case scenario in which space is at a premium.

In described implementations, however, no dedicated pressure sensor is required. Instead, an applied pressure is inferred or derived from an electrical signal, e.g., from a voltage or frequency of the electrical signal. For example, when the electrical signal includes components that are motion artifacts reflecting the pressure applied by a user associated with pressing an electrode, then described implementations calculate and quantify an existence and extent of the degree of pressure being applied to the electrode. The calculated pressure may then be used to control a device operation or other function of a device.

Consequently, described implementations enable touch pressure interactions, using, e.g., simple, small, inexpensive electrodes that may be installed and used in conjunction with a wide variety of computing devices and associated peripherals, including wearable devices. Thus, desirable and advantageous features of pressure-based controls may be obtained, including features that were previously impractical or unavailable.

Moreover, such touch pressure control may be provided in conjunction with other types of control systems and actions, using the same electrodes. For example, a pair of electrodes may be used to provide touch pressure control as referenced above, and the same pair of electrodes may be used to provide an additional function, such as providing electrocardiography (ECG) measurements.

Figure 1:
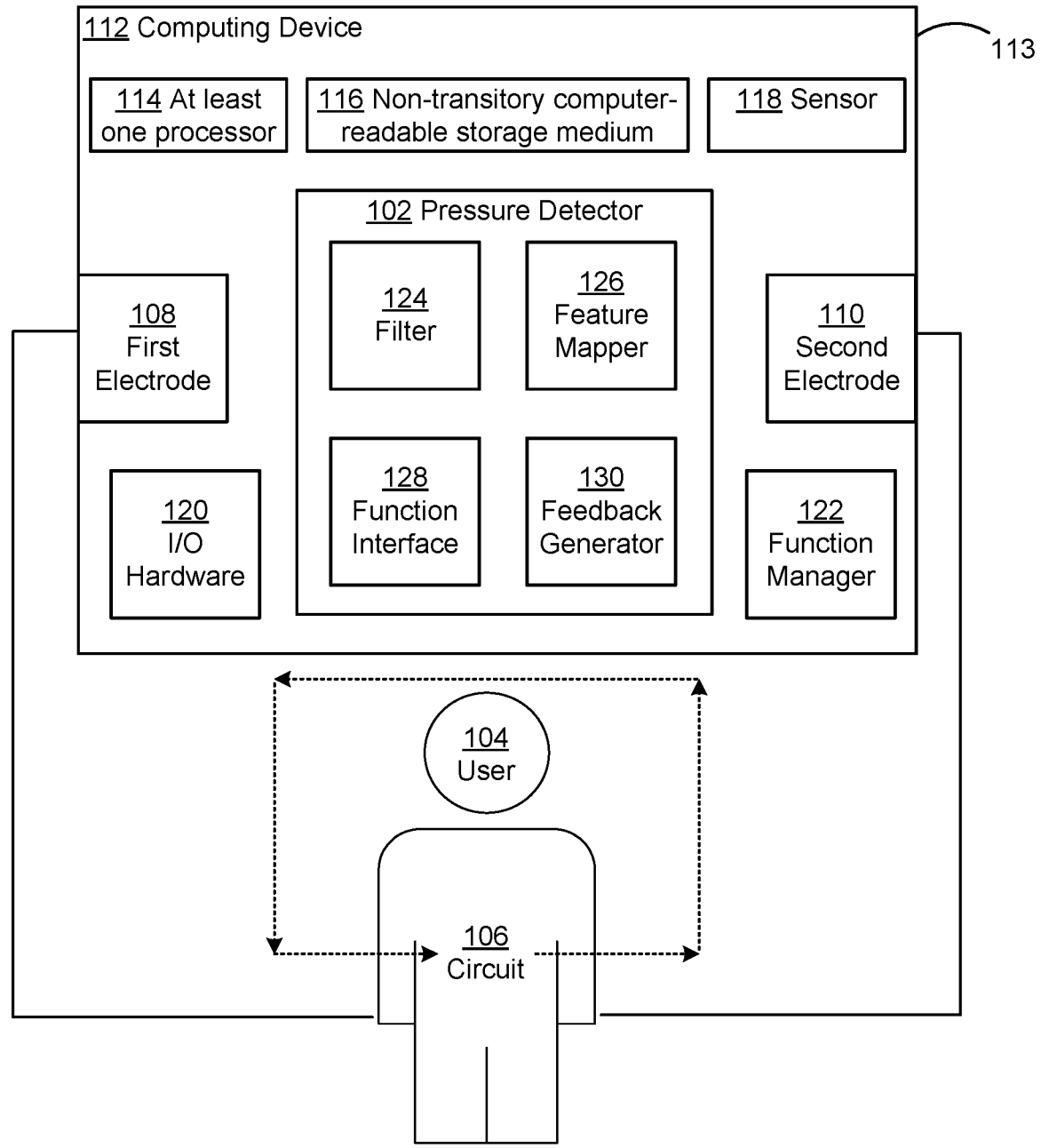
FIG. 1 is a block diagram of at least one computing device providing a touch pressure input.

FIG. 1 is a block diagram of at least one computing device 112 providing a touch pressure input. In the example of FIG. 1, a pressure detector 102 is configured to determine touch pressure applied by a user 104 when the user establishes a closed circuit 106 by simultaneously contacting, e.g., touching (with the user's skin surface) a first electrode 108 and a second electrode 110 of the at least one computing device 112, including applying pressure to at least one of the first electrode 108 and the second electrode 110. As referenced above, and described in detail below, the pressure detector 102 may be configured to determine an existence of this pressure using a measured electrical signal of the closed circuit 106, and does not require a dedicated pressure sensor to do so.

The at least one computing device 112 may include any type of computing device that includes at least one processor 114, which may be configured, among other functions, to execute instructions stored using a non-transitory computer-readable storage medium 116. A sensor 118 may be used to measure desired properties of the electrical signal of the closed circuit 106, such as current, voltage, or frequency.

As the at least one computing device 112 may represent many types of computing devices, examples of which are provided herein, the many types of input/output (I/O) hardware that may be used in such computing devices are illustrated in the aggregate in FIG. 1 as I/O hardware 120. By way of non-limiting example, such I/O hardware may include a display (e.g., a touchscreen), a peripheral device (e.g., mouse, keyboard, or stylus), a button, a speaker or audio sensor, haptic sensor or output, or camera. In some implementations, the sensor 118, the first electrode 108, and the second electrode 110 may be considered examples of the I/O hardware, but are shown separately in FIG. 1 for ease of explanation of functionality of the pressure detector 102.

In FIG. 1, the computing device 112 is illustrated as including a body 113. The electrodes 108, 110 may be mounted on the body 113 in positions accessible to a skin surface of the user 104. Examples of the body 113 may be understood from example implementations illustrated below, such as in FIGS. 5, 6, and 11-13B.

In addition to the I/O hardware 120, the at least one computing device 112 may execute and provide many types of software that utilizes, or is implemented by, the at least one processor 114, the non-transitory computer-readable storage medium 116, and the I/O hardware 120. Such software (and associated functionality) is included and represented in FIG. 1 by a function manager 122.

That is, for purposes of the description of the simplified example of FIG. 1, the function manager 122 should be understood to represent and encompass the implementation of any software that may be associated with operation of the I/O hardware 120 and/or the pressure detector 102. For example, the function manager 122 may include an operating system and many different types of applications that may be provided by the at least one computing device 112, some examples of which are provided in more detail, below.

In particular, in the examples of FIGS. 3A-5, the at least one computing device 112 may represent a wearable device, such as a smartwatch. The function manager 122 may provide the function of ECG measurements for the user 104, using signals from the first electrode 108 and the second electrode 110. Then, the same signals may be used at other times, when the ECG measurements are not being taken, to provide the types of touch pressure control described herein. In such cases, existing ECG-related elements of a smartwatch may be used to implement the touch pressure control techniques described herein, without requiring any additional hardware components to be added to the smartwatch.

More generally, in the example of FIG. 1, it may be observed that the closed circuit 106 is established as including or traversing a body of the user 104. The ability to establish such a circuit has previously been used in other contexts, such as the ECG context just referenced, because the resulting circuit and electrical signals thereof capture electrical activities of, e.g., a heart of the user 104.

In contrast, however, described techniques seek to measure, quantify, or otherwise utilize motion artifacts of such electrical signals that are superimposed on the signal characteristics reflecting the electrical activities of the heart of the user 104. In other words, as described and illustrated in detailed examples below with respect to FIGS. 6-8, actions of the user 104 in applying pressure, e.g., to the first electrode 108 when the circuit 106 is closed, will cause corresponding distortions of the electrical signal reflecting the electrical activities of the heart of the user 104.

Then, the pressure detector 102 may be configured to measure such distortions, or motion artifacts, and relate the distortions to an existence and extent of the pressure applied by the user 104 to the first electrode 108. For example, such relations may be determined heuristically. In other examples, such as described below with respect to FIGS. 8 and 9, a trained machine learning model may be configured to classify specific patterns in electrical signals of the closed circuit 106 as corresponding to specific, pre-defined levels of pressure applied by the user to one or both of the first electrode 108 and the second electrode 110.

For example, in FIG. 1, the pressure detector 102 is illustrated as including a filter 124. The filter 124 may be configured to remove portions of the electrical signal detected by the sensor 118, in order to make the resulting, filtered signal more amenable to analysis by a feature mapper 126. For example, when the electrical signal contains a heart electrical activity component of the user 104, which may be a dominant feature as compared to the motion artifacts utilized by the pressure detector 102, the filter 124 may be configured to remove this heart electrical activity component.

Then, a feature mapper 126 may be configured to analyze the resulting, filtered signal, and map characteristics thereof to corresponding levels of pressure applied by the user 104. For example, the feature mapper may obtain spectral features from a voltage signal measured by the sensor 118. Then, as just referenced, the feature mapper 126 may use either a heuristic or machine learning approach to mapping resulting spectral features to levels of pressure applied by the user 104.

Once these pre-defined levels of pressure are determined, then a function interface 128 may provide the determined levels of pressure to the function manager 122. The function manager 122 may thus implement any preconfigured use of the detected pressure levels to operating software or other hardware of the at least one computing device 112.

For example, the determined pressure levels may be used to implement discrete functions, such as activating or deactivating a specific application or application feature, or selecting one application or another for use. In other examples, the determined pressure levels may be determined to finer levels of gradation, or as continuously-changing pressure levels. Such pressure levels may be used in corresponding contexts that would benefit from this type of control, such as increasing/decreasing a brightness a screen, or a volume of a speaker.

A feedback generator 130 may be configured to provide the user 104 with feedback regarding a detection and characterization of the pressure being applied by the user 104, so that the user 104 may provide necessary levels or types of pressure, and obtain desired results with respect to operating the at least one computing device 112. For example, the feedback generator 130 may leverage specific elements of the I/O hardware 120 to provide a feedback signal of varying sorts. For example, the I/O hardware 120 may include a vibration generator, and the feedback generator 130 may cause such a vibration generator to vibrate at levels that are directly proportional to pressure levels determined by the feature mapper 126. In other examples, other types of feedback may be provided for similar purposes, including audio and/or visual feedback.

In example implementations, one of the first electrode 108 and the second electrode 110 may be referred to as a passive electrode, which is maintained in a default state of contact with the user 104 during a normal use of the at least one computing device 112. For example, when the at least one computing device 112 includes a smartwatch, as in the examples of FIGS. 3A-5, below, the first electrode 108 may be provided on an underside of the smartwatch, and in contact with a wrist of the user 104 during normal wear of the smartwatch. Then, the second electrode 110 may be provided as a button that is accessible for pressing by the user 104, in order to complete the closed circuit 106.

Thus, in example implementations, the circuit 106 may be maintained in a default open state, and may be closed when the user 104 contacts, and applies pressure to, the second electrode 110. In example implementations in which the first electrode 108 is referred to as a passive electrode, the second electrode 110 may be referred to as an active electrode. As described in more detail, below, three or more electrodes may be used, including two or more passive electrodes and/or two or more active electrodes.

Similar configurations of passive and active electrodes may be implemented in other types of devices. For example, the at least one computing device 112 may be implemented as a pair of smart glasses, such as virtual reality (VR) or augmented reality (AR) glasses. Then, the first electrode 108 may be positioned at a point on the glasses that rests on, and is in contact with, a nose of the user 104, while the second electrode 110 may be positioned at one side (e.g., temple, or glasses arm) of the glasses.

Similar implementations may be provided with respect to earbuds. For example, one earbud may be provided with the first electrode 108 contacting a user's ear when resting therein or thereon, while the other earbud may have the second electrode 110 exposed for pressing by the user 104.

In other types of implementations, both of the first electrode 108 and the second electrode 110 may be in a default open state (e.g., may both be referred to as active electrodes), and the user 104 may be required to touch the first electrode 108 with one hand (e.g., the user's left hand), and the second electrode 110 with the other hand (e.g., the user's right hand). For example, the at least one computing device 112 may represent a smartphone, and the user 104 may hold the smartphone in one hand, while contacting the first electrode 108 with that hand, and may then apply pressure to the second electrode 110 with the other hand.

Similarly, in the smart glasses implementations referenced above, the first electrode 108 may be positioned at one side (e.g., temple, or glasses arm), while the second electrode 110 may be positioned at the opposite side of the glasses. Also, in the earbuds example, the first electrode 108 may be positioned at one earbud, while the second electrode 110 may be positioned at the other earbud.

As a result, in these and other example implementations, by applying pressure to obtain desired functionality, the user 104 may be provided with the feel of physically pushing an icon or other selected item of, or onto, a display of a device. Such a pushing feel may be enhanced by making the degree of pressure applied proportional to a speed of reaction of the display. For example, when scrolling through a large number of icons (e.g., apps), the user may scroll faster by applying more pressure, or scroll slower by applying less pressure.

Thus, described implementations provide many features, advantages, uses, and functionalities that would be difficult, impractical, infeasible, or impossible to achieve using conventional techniques for device control, including conventional pressure sensors. Moreover, users may be provided with abilities to control devices in convenient and intuitive manners.

Figure 2:
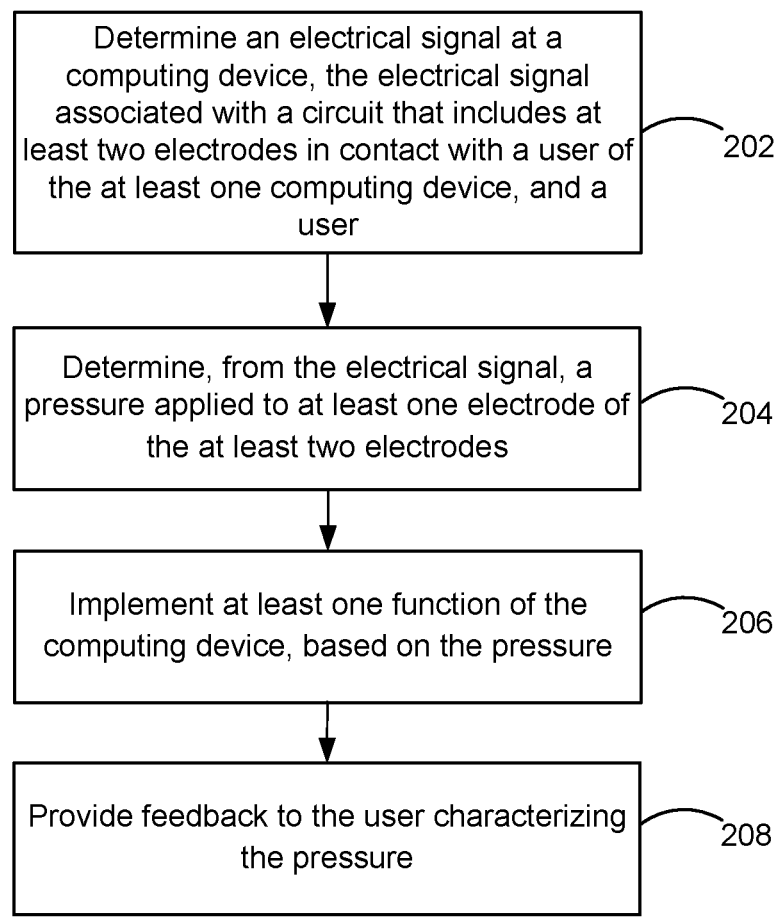
FIG. 2 is a flowchart illustrating example operations of the system of FIG. 1.

FIG. 2 is a flowchart illustrating example operations of the system of FIG. 1. In the example of FIG. 2, operations 202-208 are illustrated as separate, sequential operations. However, in various example implementations, the operations 202-208 may be implemented in an overlapping or parallel manner, and/or in a nested, iterative, looped, or branched fashion. Further, various operations or sub-operations may be included, omitted, or substituted.

In FIG. 2, an electrical signal may be determined at a computing device, the electrical signal associated with a circuit that includes at least two electrodes in contact with a user of the computing device, and a user (202). For example, the pressure detector 102 may determine the electrical signal from the circuit 106 when the user 104 closes the circuit 106 by contacting both the first electrode 108 and the second electrode 110. A voltage of the electrical signal may be measured, using, e.g., the sensor 118.

As described, the at least one computing device may include any computing device which may benefit from the types of touch pressure input described herein, including laptops, tablet computers, smartphones, smartwatches, smart glasses, earbuds, and other wearable devise. Other examples of types of devices may include cameras, kiosks, cooking appliances, and various other types of appliances.

In some implementations, one or more of the at least two electrodes may be installed on a peripheral device, such as a keyboard, mouse, or stylus. In some such implementations, processing and storage hardware may be maintained on a separate device, in wired or wireless communication with the peripheral device.

In the above and other types of example implementations, three or more electrodes may be used. For example, a single passive electrode may be used, and two or more active electrodes may be used. In this way, for example, each of the two or more active electrodes may have a dedicated function(s). Similarly, two passive electrodes and two active electrodes may be provided. For example, in implementations using earbuds, each earbud may have a passive and active electrode, so that the user 104 may experience one set of functionality when applying pressure to one active electrode in one ear (through establishing the circuit 106 with the passive electrode in the opposite ear), while experiencing another set of functionality when applying pressure to the other active electrode in the opposite ear (through establishing another instance of the circuit 106 with the passive electrode in the first ear).

From the electrical signal, a pressure applied to at least one electrode of the at least two electrodes may be determined (204). For example, the pressure detector 102, having determined the electrical signal using the sensor 118, may filter the received signal using the filter 124. For example, as described herein, the circuit 106 may include a large component related to internal electrical activity of the user 104, such as electrical heart activity of a heart of the user 104. Such components may dominate, e.g., may be significantly larger than, motion artifacts resulting from pressure applied by the user 104 to the active electrodes.

By removing these components, the filter 124 may enable the feature mapper 126 to map features of the electrical signal to corresponding pressure levels more accurately. For example, a measured voltage signal may be analyzed to determine corresponding frequency characteristics (which may be referred to herein as spectral features). Then, the feature mapper 126 may map the determined spectral features to corresponding pressure levels, using, e.g., previously-determined heuristics, or a previously-trained machine learning model, as described in more detail, below.

At least one function of the computing device may be implemented, based on the pressure (206). For example, the function interface 128 may communicate with the function manager 122 to implement virtually any available function of the at least one computing device 112.

As described herein, such functionality may be dedicated, such as when pressing the second electrode 110 provides a dedicated, pre-configured function. In other examples, the functionality may be configurable by the user 104, such as when the user 104 can designate a desired function to be performed in response to application of pressure to the second electrode 110. In some implementations, the functionality may vary by context. For example, the functionality providing in the context of one application may be different than the functionality provided in another context.

In some implementations, the at least two electrodes may provide additional functionality, beyond the touch pressure input techniques provided herein. For example, the function manager 122 may provide an ECG measurement function and related applications. When the at least one computing device 112 (e.g., smartwatch) is in an ECG mode, the electrodes 108, 110 may be used to provide ECG measurements, related to the electrical heart activity of the user 104. In such implementations, the motion artifacts used by the pressure detector 102 may be filtered out of the electrical signal measured using the first electrode 108 and the second electrode 110, as such motion artifacts and any other signal components may be considered to be noise for purposes of providing ECG measurements or other measurements related to the electrical heart activity of the user 104.

Finally in FIG. 2, feedback may be provided to the user, characterizing the pressure (208). For example, the feedback generator 130 may provide visual, audio, or haptic indicators to the user 104. For example, such indicators may vary in direct proportion to an amount of pressure applied to the second electrode 110. For example, visual indicators may vary in brightness or displayed size, and audio or haptic indicators may also vary in extent in proportion to the determined pressure. Using such feedback, the user 104 may easily determine whether it is necessary to apply more or less pressure to achieve a desired result with respect to the functionality being provided.

Figures 3, 4:
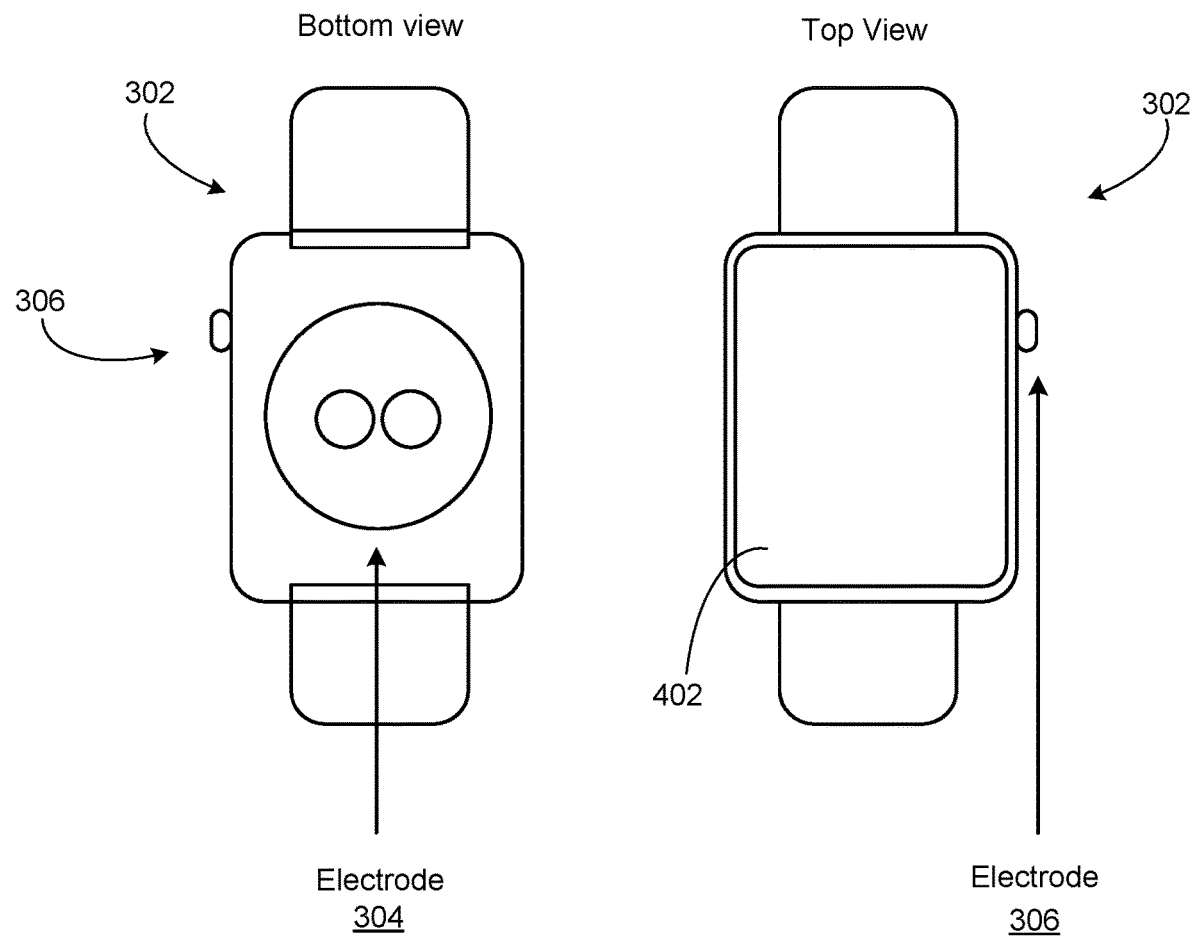
FIG. 3 illustrates a bottom view of a wearable device providing a touch pressure input, in accordance with example implementations of FIG. 1.
FIG. 4 illustrates a top view of a wearable device providing a touch pressure input, in accordance with example implementations of FIG. 1.

FIG. 3 illustrates a bottom view of a wearable device providing a touch pressure input, in accordance with example implementations of FIG. 1. FIG. 4 illustrates a top view of the wearable device of FIG. 3. Specifically, FIGS. 3 and 4 illustrate a smartwatch 302, which has a first electrode 304 positioned on a surface of the smartwatch 302 that would typically be in contact with a skin surface of the user 104 when the smartwatch 302 is being worn by the user 104.

As referenced above, the electrode 304 may thus represent an example of a passive electrode. As also illustrated, the electrode 304 may be provided with a surface area that is as large as practicable relative to available surface area of the smartwatch 302. Accordingly, a reliability of a contact of the electrode 304 with a skin surface of the user 104 may be increased.

Meanwhile, an electrode 306 may be implemented as a button or similar shape. That is, the electrode 306 may be a simple metal electrode, and it not required to have any separate or additional mechanical functioning, such as a spring-loading mechanism. Nonetheless, as the electrode 306 may provide a desired electrical contact in any shape desired, the implementation of FIGS. 3 and 4 illustrate that the electrode 306 may be implemented in a shape resembling a button for ease and familiarity of use of the user 104. More generally, as shown and described with respect to the additional example implementations of FIGS. 11-14, either of the electrodes 304, 306 may be sized, shaped, or positioned in virtually any desired manner to achieve a desired user interaction.

As shown in the top view of FIG. 4, the smartwatch includes a display 402 that may provide any conventional or future features available in the context of a smartwatch, including access to applications, messages, or other features or content. When seen from the top view of FIG. 4, it may be observed that the user 104 is provided with the display 402 and the electrode 306, and may operate the electrode 306 as a pressure-sensitive button, without being required to take further action with respect to the electrode 304.

Figure 5:
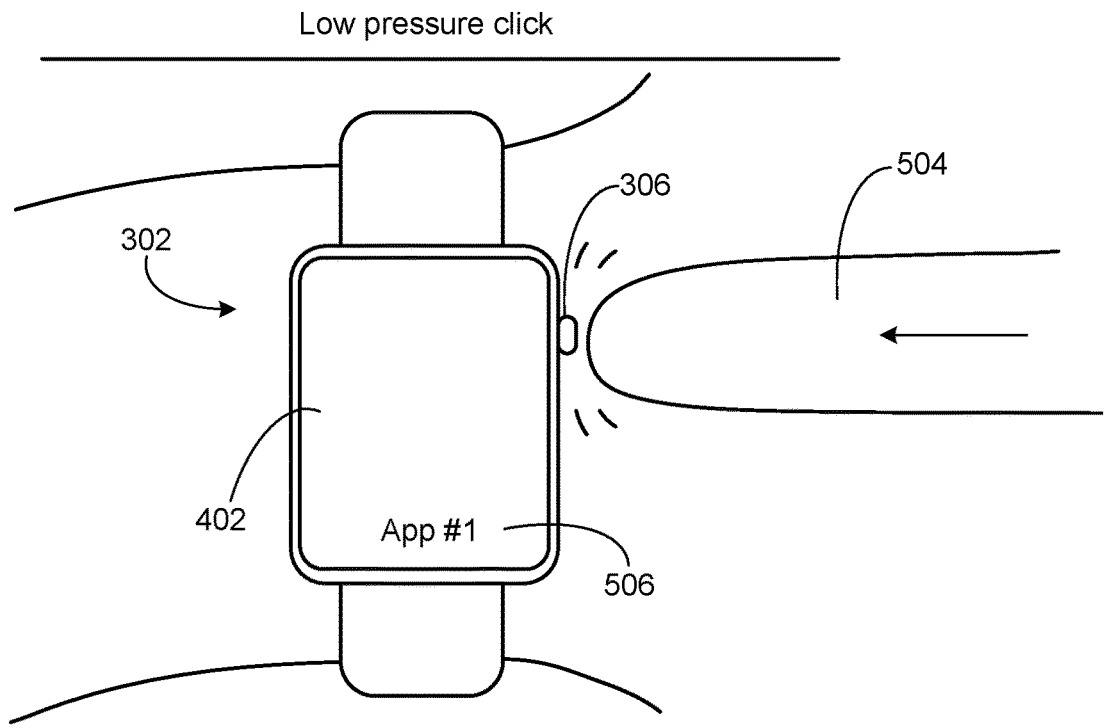
FIG. 5 illustrates a first use case example of the wearable device of FIGS. 3A and 3B.

For example, in FIG. 5, the smartwatch 302 is illustrated as being worn on a wrist 502 of the user 104, and the electrode 306 is illustrated as being pushed or pressed by a finger 504 of the user 104. As already described, the finger 504 contacting (e.g., pressing) the active electrode 306, while the passive electrode 304 is contacting the wrist 502 (of the other arm of the user 104) completes the circuit 106 of FIG. 1, so that an electrical signal traversing the body of the user may be determined and used to identify and characterize a pressure being applied to the active electrode 306.

In the example of FIG. 5, it is assumed that a low pressure click is applied by the finger 504 and detected by the pressure detector 102 of FIG. 1. Such a low pressure click may be configured to cause a function related to an illustrated application 506 (such as a selection thereof).

Figure 6:
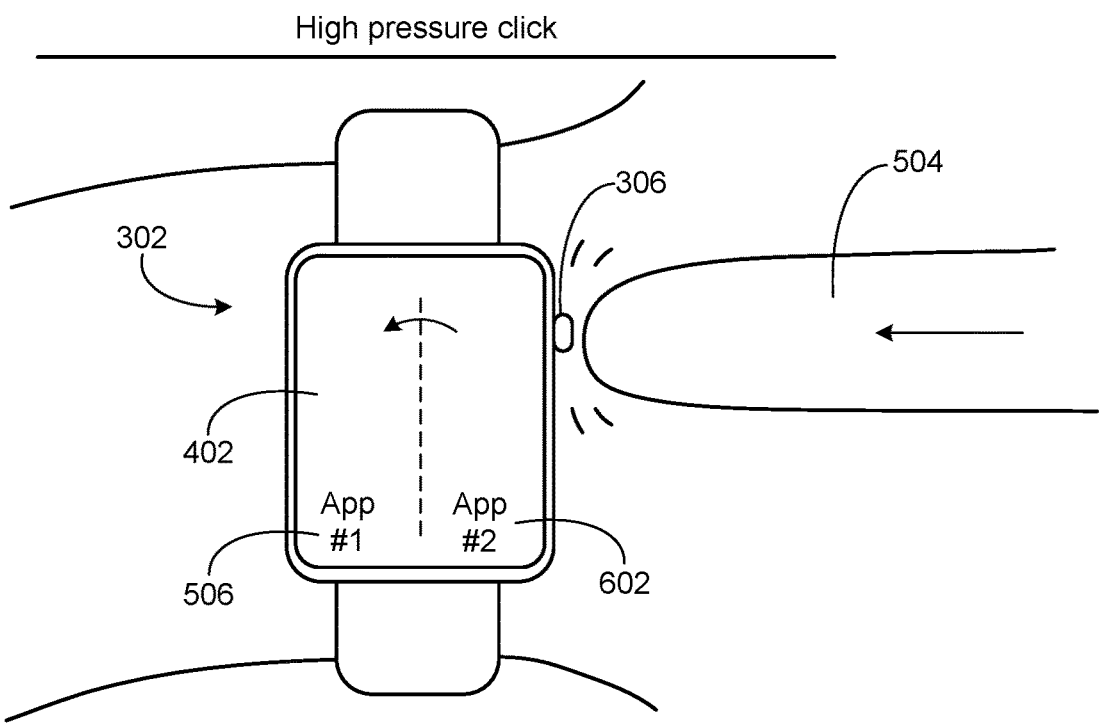
FIG. 6 illustrates a second use case example of the wearable device of FIGS. 3A and 3B.

In FIG. 6, a high pressure click may be applied, which may be configured to cause a different function. For example, as shown, the high pressure click of the active electrode 306 may cause the application 506 to slide to the left of the display 402, and may cause a second application 602 to be displayed as available for selection. Consequently, the user 104 may have a physical sensation or perception of pushing the application 506 to the left to access or use the application 602, and consistent with a direction of pressure of the finger 504 on the active electrode 306.

Smartwatches are able to serve as a convenient gateway for many communication routines with connected smartphones, including, e.g., notifications and text messaging. However, conventional smartwatches lack the richness in human interaction mechanics, compared to smartphones. For example, smartwatches typically do not have a large touch display nor various sensors to fit in a small form factor.

Described techniques effectively provide a pressure click, in which an active electrode, like the active electrode 306, provide a physical button and associated software that is capable of sensing the pressure of a user's finger click, so that depending on the pressure level, an appropriate routine can be triggered. For example, as shown in FIGS. 5 and 6, a level of external pressure applied by a click may be configured to be directly proportional to a location in the display 402 in which an apps menu is being localized. As described, to the user 104, the navigation through the apps menu may feel as though the apps 506, 602 are being physically pushed to the side from one to next.

As also referenced above with respect to FIG. 1, some otherwise-conventional smartwatches have electrocardiography (ECG) modules that can measure sinus rhythms and even screen atrial fibrillation (AFib) for users interested in health monitoring. For example, the examples of FIGS. 3-6 may be used, in which a lead-I ECG technique is used with one electrode below the smartwatch touching the wrist skin and another electrode located at the watch crown, so that when the user touches the crown with a finger of the other hand, a closed circuit is formed between the smartwatch and the heart to measure electrical activities of the heart.

In some example implementations, an existing ECG module in a smartwatch may be leveraged to measure pressure levels for flexible human-smartwatch interactions, as described herein. For example, in FIG. 7, a first pressure 702 applied may result in a first signal 704, a second pressure 706 applied may result in a second signal 708, and a third pressure 710 applied may result in a third signal 712. For example, the pressures 702, 706 and 706, 710 may vary by a factor of about 2-3.

As shown, heartbeats 714, 716, 718 may be detected in the resulting electrical signals 704, 708, 712. Additionally, motion artifacts 720 may be observed. As shown, the motion artifacts 720 are appreciably smaller than the heartbeats 714, 716, 718, but increase (e.g., in magnitude and/or frequency) in direct proportion to a degree of pressure applied to the active electrode 306.

Thus, by observing the motion artifacts 720 that are present in the ECG signals 704, 708, 712, a robust pressure sensing model may be generated based on the illustrated fact that different external pressures result in different ECG motion artifact characteristics. Conventionally in the context of ECG measurements, such ECG motion artifacts are to be completely avoided and rejected in hardware or in algorithms as they do not contain, or may obscure, useful information about the heart condition that is desired. However, described techniques use this traditional noise signal as a pressure input that enhances human-smartwatch interactions by deviating away from its original cardiovascular health use cases, and thereby opening up new, powerful interaction routines for a smartwatch user. For a smartwatch that already provides an ECG module, such interaction routines may be realized with little or no additional hardware, and merely by utilizing existing ECG components.

In more detail, conventional smartwatches with ECG functionality effectively miniaturize an on-body lead-I ECG setup used in healthcare settings, so that two electrodes that are clipped at two sides of the chest in the healthcare setting are ported to left and right hands of a user to obtain a closed circuit between the smartwatch and the user's heart, such as illustrated in FIG. 1. The resulting ECG signal(s), such as the signals 704, 708, 712, may be measured in millivolts and has a known template (PQRST) for a heartbeat. This template contains information about the size and position of the heart chambers, illustrated by the heartbeat portions 714, 716, 718 of the signals 704, 708, 712, respectively. As also described, the motion artifacts 720 typically are considered to be contaminants in a conventional ECG measurement context. In described techniques, however, such motion artifacts contain and represent finger pressure applied by the finger on the ECG electrode. The harder the press is, the noisier the raw ECG signal becomes, and described techniques utilize this finger press sensitivity to infer click strength.

Figure 7:
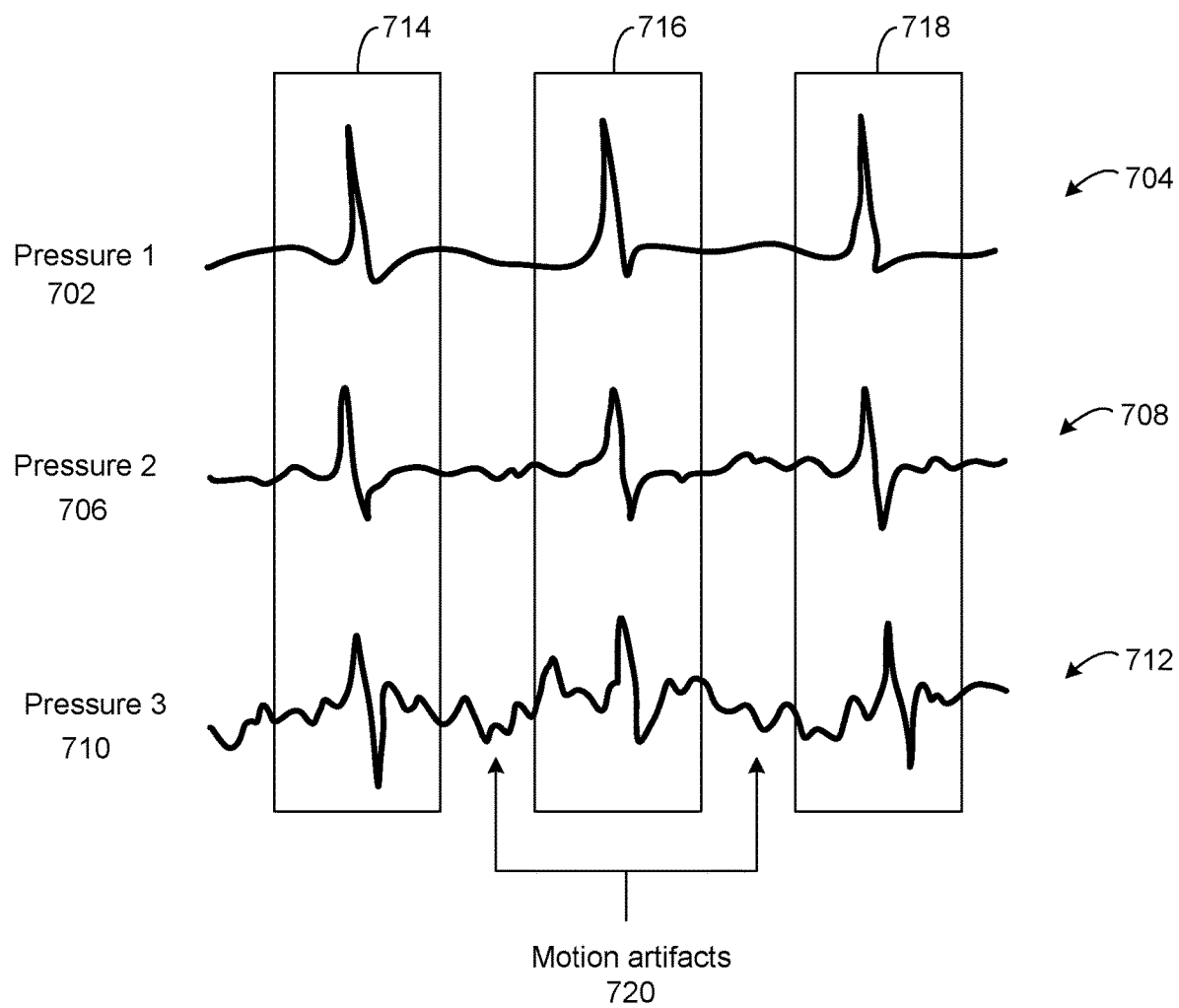
FIG. 7 illustrates example voltage signals that may be used to determine pressure, in accordance with example implementations of FIG. 1.
Figure 8:
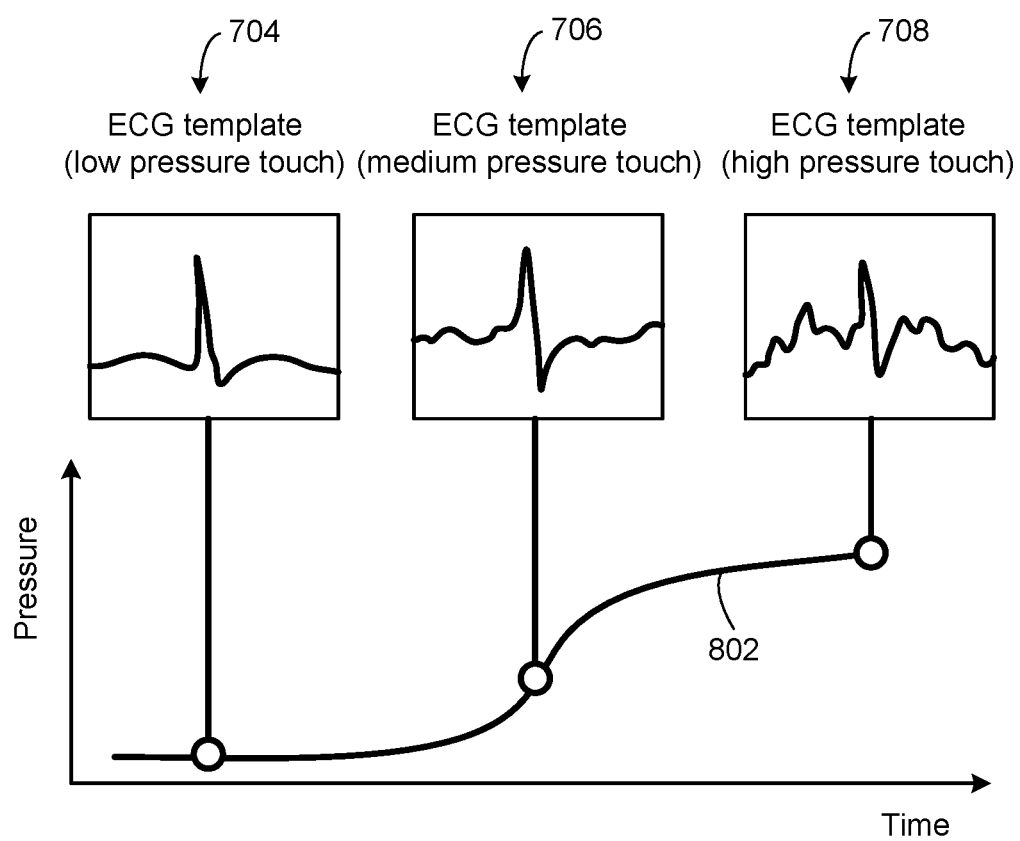
FIG. 8 illustrates example relationships between the voltage signals of FIG. 7 and corresponding levels of pressure, in accordance with example implementations of FIG. 1.

FIG. 8 illustrates example relationships between the voltage signals of FIG. 7 and corresponding levels of pressure, in accordance with example implementations of FIG. 1. As shown, a pressure signal 802 over time may be generated which is inferred from, and correspond to, the signals 704, 706, 708. That is, FIG. 8 illustrates an example of how output pressure corresponds to different noise levels (including micromotion artifacts) of an ECG input signal.

As shown, the signal 704 relates to a first pressure level of the pressure signal 802, e.g., a low pressure touch. The signal 706 relates to a second pressure level of the pressure signal 802, e.g., a medium pressure touch. The signal 708 relates to a third pressure level of the pressure signal 802, e.g., a high pressure touch.

Figure 9A:
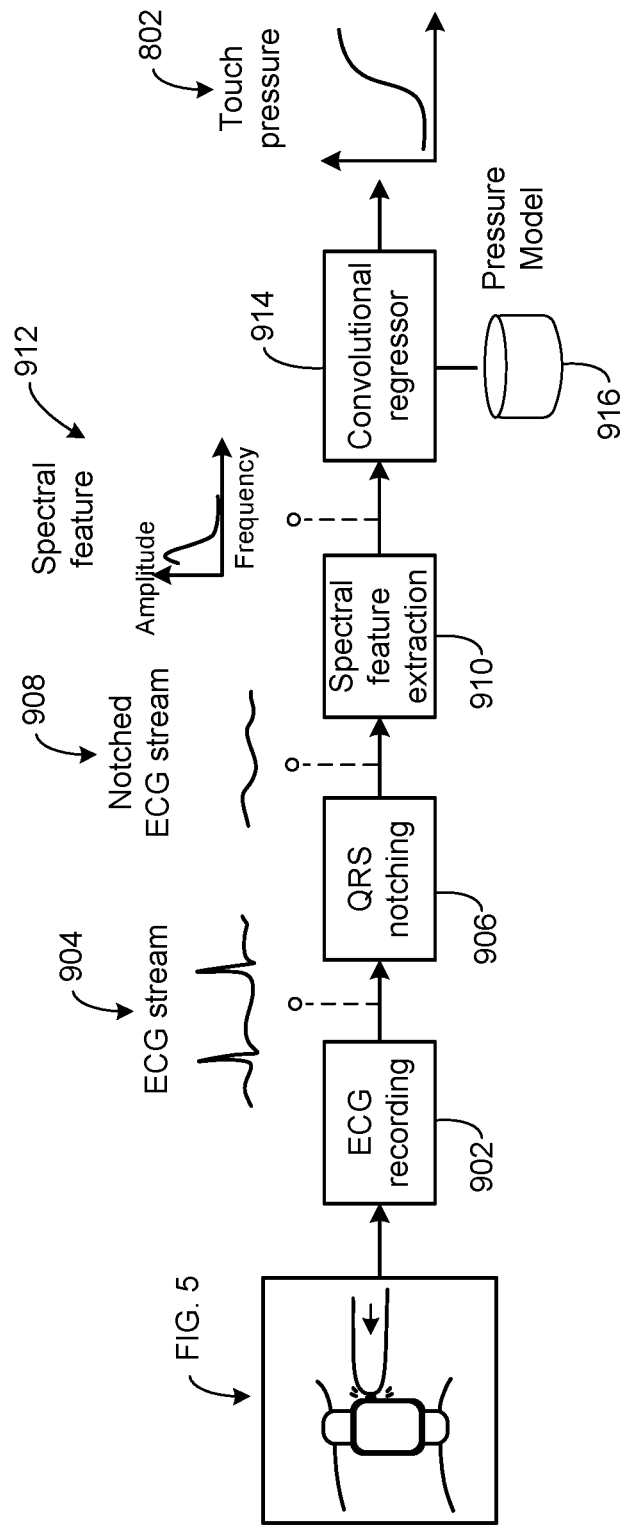
FIG. 9A is a flowchart illustrating detailed example operations of the wearable device of FIGS. 3-6, using the voltage signals of FIGS. 7 and 8.

FIG. 9A is a flowchart illustrating detailed example operations of the wearable device of FIGS. 3-6, using the voltage signals of FIGS. 7 and 8. In FIG. 9A, an ECG recording (902) of a raw ECG signal 904 may be obtained from a touch pressure input, such as described above with respect to FIG. 5, e.g., when the user 104 touches the smartwatch at a designated electrode.

In the context of ECG measurements, a QRS complex refers to deflections in an electrocardiogram (ECG) tracing, and represent ventricular activity of a user's heart. That is, a QRS complex includes Q, R, and S waves and represent a heart's electrical impulse spreading through the ventricles of the user's heart. QRS waves are part of the PQRST template for a heart beat, and QRS notching (906) refers to adaptive filtering of such electrical signals from the user's heart, using, e.g., an inverse matched filter. In this way, a notched ECG stream 908 may be obtained.

The notched ECG stream 908 thus corresponds to a noise level signal, on which spectral feature extraction (910) may be performed to describe frequency contents and characteristics of the notched ECG stream 908. In this way, spectral features 912 are obtained.

Figure 9B:
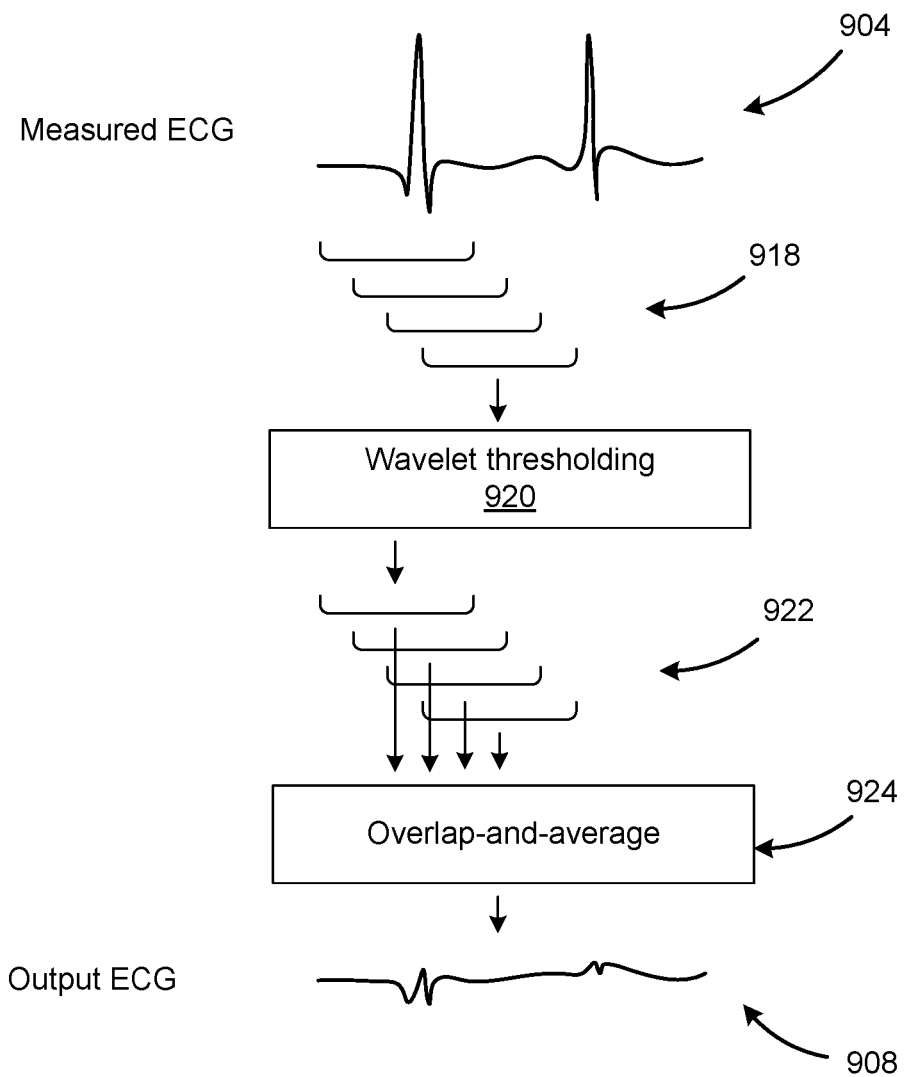
FIG. 9B is a block diagram of an example filtering operation of FIG. 9A.

FIG. 9B illustrates a more detailed example of the QRS notching 906 of FIG. 9A. In FIG. 9B, a sliding window 918 scans through the measured ECG stream 904. Each window contains N samples of the ECG stream 904. Each window independently goes through a wavelet thresholding procedure 920. Such wavelet thresholding works well with the ECG peak, which is (extremely) time-concentrated. Frequency-based filtering techniques may also be used, but may be less suitable to separate peak from non-peak signal as well as the described example. That is, the described wavelet-based techniques are more time-frequency neutral, and can accomplish peak notching without shaving off the motion artifacts described herein. Once the thresholding operation 920 is done, the overlapping windows 922 are stitched back using an overlap-and-average operation 924 to represent a time series with QRS peaks notched out, shown as output, notched ECG stream 908.

A pressure model 916 may then be used to perform convolutional regression (914) on the spectral features 912, to thereby obtain the pressure signal 802 of FIG. 8. That is, for example, a convolutional neural network may be trained, using sufficient quantities of training data, to accurately map the spectral feature 912 to the pressure signal 802.

For example, tests may be run using one or more pressure sensors to measure actual pressure levels being applied by users, in conjunction with corresponding pressures applied to ECG electrodes. In this way, the micromotion artifacts of the measured ECG signals may be correlated with the corresponding pressures.

Figure 10A:
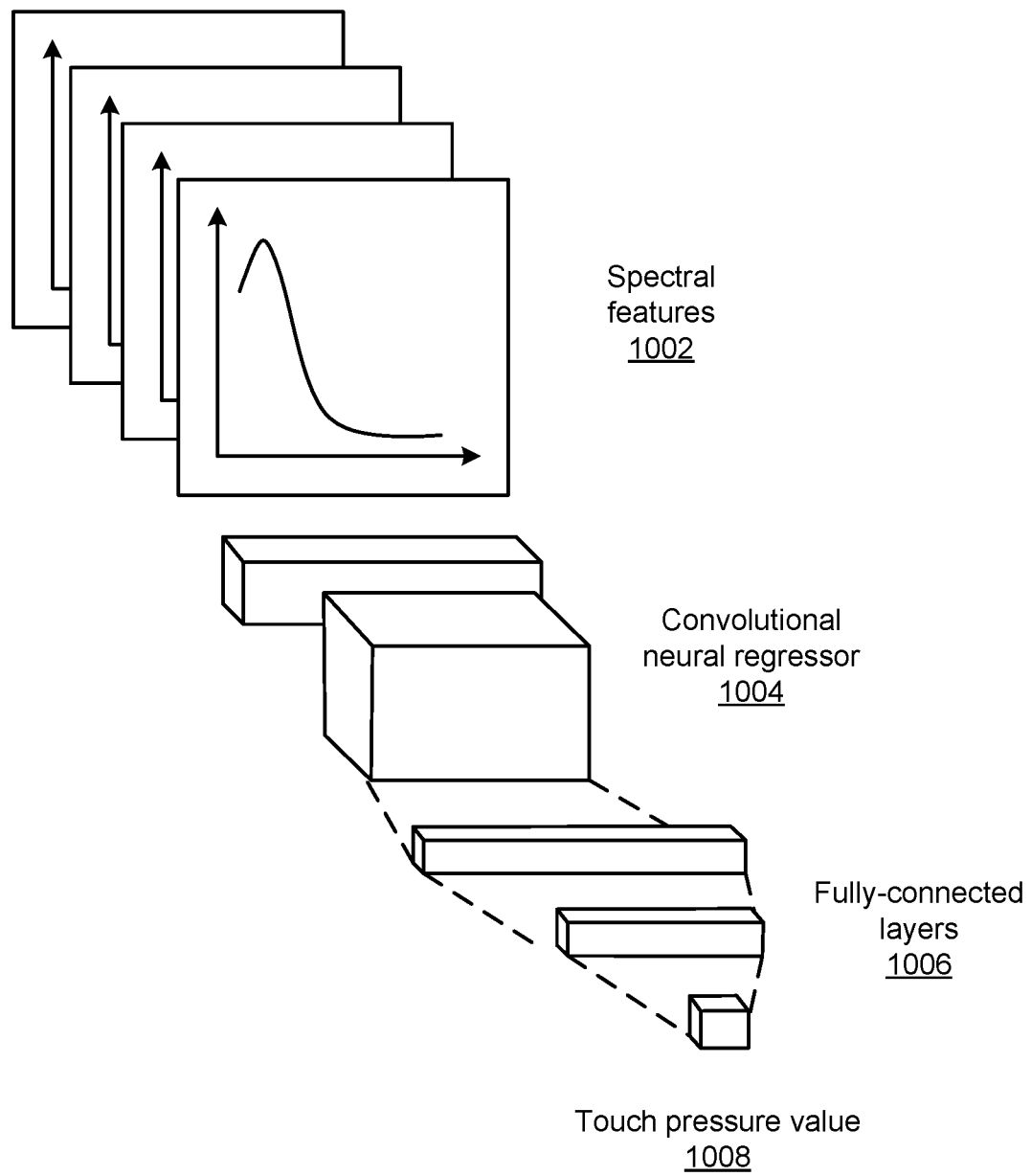
FIG. 10A illustrates an example machine learning algorithm that may be used to related a voltage signal with motion artifacts to a touch pressure value, in accordance with example implementations of FIGS. 1 and 9A.

For example, FIG. 10A illustrates an example machine learning algorithm that may be used to relate a voltage signal with motion artifacts to a touch pressure value, in accordance with example implementations of FIGS. 1,9A, and 9B. As shown in FIG. 10A, spectral features 1002 may be passed through a convolutional neural network 1004 (including one or more convolutional layers), and corresponding fully-connected layers 1006, to obtain a corresponding touch pressure value 1008. That is, a convolutional neural network may be used as a regression model to determine the mapping from a spectral feature to a pressure level. The model may be used to provide a common set of weights during runtime for all users.

In particular, N may equal any value that may be obtained with sufficient quantity and quality of training, so that the user 104 may be provided with a virtually continuous spectrum of pressure levels. In one example, a fully-connected layer 1006 takes an assigned input volume from a preceding layer, and outputs an N dimensional vector, where N is a number of classes available for assigning pressure levels. In other words, as referenced above with respect to FIG. 8, pressure levels may be assigned to one, two, three, or more values, such as low, medium, or high. In the latter case, if N=3, then the three classes of low, medium, high may be available for designation.

In other examples, as also referenced, pressure levels may be determined heuristically, without requiring the training and use of a machine learning model. For example, voltage values and/or spectral features may be associated with corresponding threshold levels, so that values above a certain threshold are interpreted as high pressure touches, while values below the threshold are interpreted as low pressure touches. Multiple thresholds may be used to obtain multiple pressure levels.

Figure 10B:
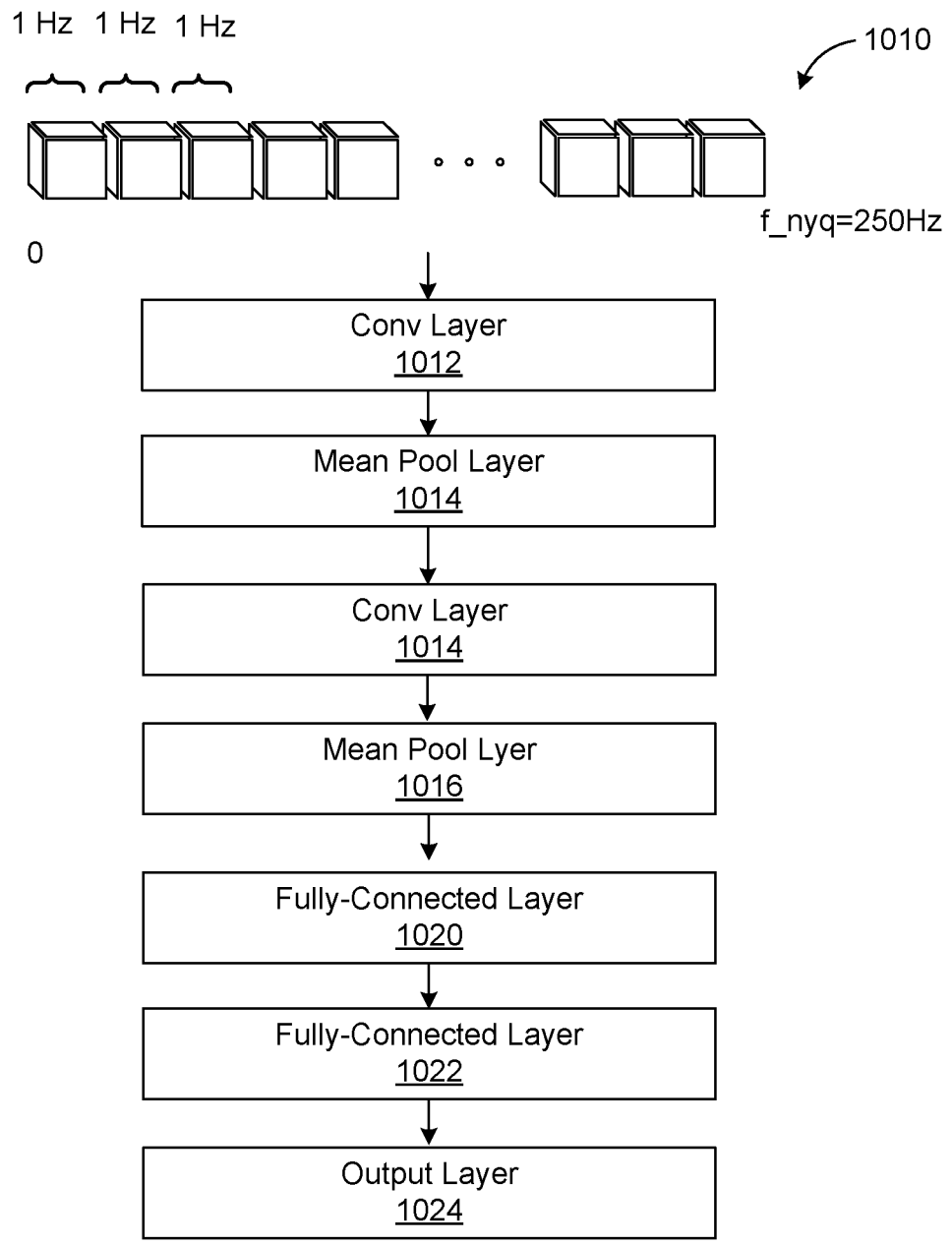
FIG. 10B is a block diagram of an example implementation of a convolutional neural regressor of FIG. 10A.

FIG. 10B is a block diagram of an example implementation of a convolutional neural regressor of FIG. 10A. FIG. 10C is a table illustrating example parameters of the example of FIG. 10B. In FIG. 10B, the spectral feature 912 of the notched ECG signal 908 enters a convolutional neural network (such as the example convolutional neural regressor 914 of FIG. 9A) to estimate a final pressure number. In an example, if a frame rate for ECG is 500 Hz, the Nyquist theorem may be used to select a spectral feature with 250 Hz cap frequency. Fast fourier transform parameters may be selected to provide a frequency feature as a 250 dimensional vector 1010, with each frequency bin containing amplitude information for a 1 Hz frequency slice.

The example convolutional neural network architecture of FIG. 10B illustrates two convolutional layers 1012, 1016, and average pooling layers 1014, 1018, as well as two fully-connected layers 1020, 1022. The convolutional layers 1012, 1016 are configured to summarize spatially-coherent information hidden in the frequency domain feature 1010. The pooling layers 1014, 1018 reduce a dimensionality (number of parameters) of features present in regions of the convolutional layers 1012, 1016. The fully-connected layers 1020, 1024, as described above, relate features of the mean pool layer 1018 to a particular class, so that the output layer 1024 may generate a corresponding pressure value.

An example size of a regressor model is given in table 1026 of FIG. 10C. Column 1028 illustrates example layers, including the layers of FIG. 10B. Column 1030 provides example output shapers of the layers 1028, and column 1032 provides example numbers of parameters of each layer. As shown in section 1034, about 7.6 k of free parameters may be sufficient to be trained and frozen offline, and used in production using scaled in-lab datasets. The resulting parameters may be stored in a permanent memory of a device, such as the various example devices of FIGS. 5, 6, and 11-13B.

Figure 11:
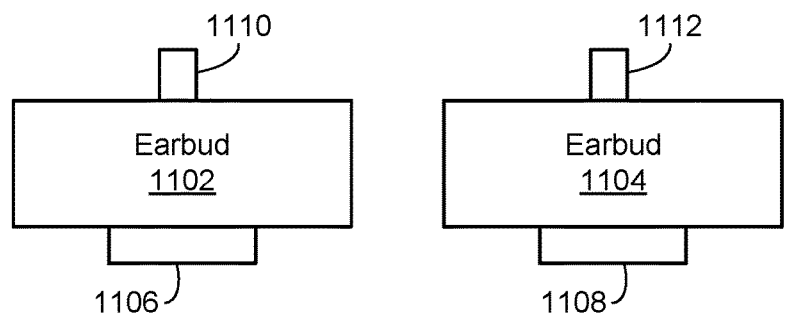
FIG. 11 is an example illustration of the system of FIG. 1, implemented using earbud devices.

FIG. 11 is an example illustration of the system of FIG. 1, implemented using earbud devices. In FIG. 11, an earbud 1102 and an earbud 1104 each have a passive electrode 1106 and a passive electrode 1108, respectively. The earbud 1102 also has an active electrode 1110, and the earbud 1104 has an active electrode 1112.

As referenced above, when wearing the earbuds 1102, 1104, the user 104 may have each of the passive electrodes 1106, 1108 in a default state of contact with the user's ear. Therefore, pressing the active electrode 1112 will complete a circuit with the passive electrode 1106 on the other side of the user's body, and may be used to perform a first function, or set of functions. Similarly, pressing the active electrode 1110 will complete a circuit with the passive electrode 1108 on the other side of the user's body, and may be used to perform a second function, or set of functions.

Figure 12:
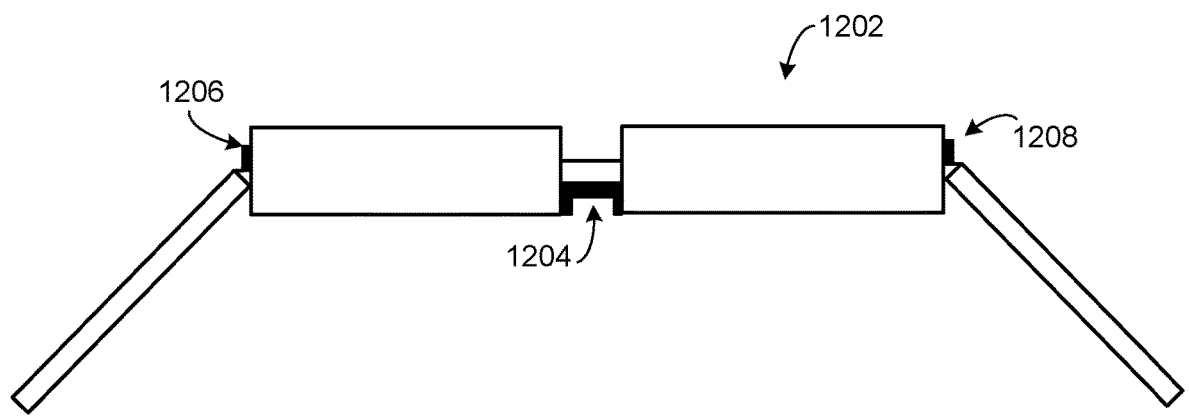
FIG. 12 is an example illustration of the system of FIG. 1, implemented using smartglasses.

FIG. 12 is an example illustration of the system of FIG. 1, implemented using smartglasses 1202. In FIG. 12, passive electrode 1204 is located on the smartglasses 1202 to rest on, and maintain contact with, a bridge of a user's nose. Then, an active electrode 1206 may be pressed to complete a circuit as described herein and obtain a first set of functions. Additionally, another active electrode 1208 may be pressed to complete a circuit as described herein and obtain a second set of functions.

In some implementations of both FIGS. 11 and 12, sufficient computing resources may be provided within the earbuds 1102, 1104 and the smartglasses 1202 to implement some or all of the pressure detector 102 of FIG. 1, and related hardware and software. In other implementations, the earbuds 1102, 1104 and/or the smartglasses 1202 may be in wired or wireless communication with another device having sufficient computing resources to implement some or all of the pressure detector 102 of FIG. 1, and related hardware and software. For example, the earbuds 1102, 1104 may be in communications with the smartglasses 1202, or either or both of the earbuds 1102, 1104 and the smartglasses 1202 may be in communication with a smartphone or other computing device.

Figure 13A:
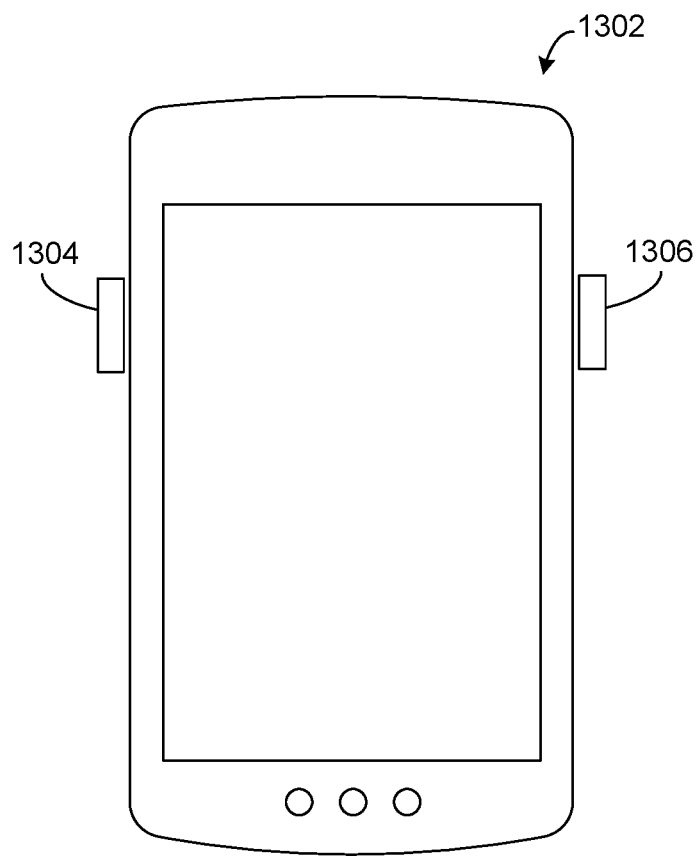
FIG. 13A is an example illustration of the system of FIG. 1, implemented using a smartphone.

FIG. 13A is an example illustration of the system of FIG. 1, implemented using a smartphone 1302. That is, in addition to providing support for wearable devices such as the smartwatch of FIGS. 3-6, the earbuds of FIG. 11, and the smartglasses of FIG. 12, the smartphone 1302 may be used to implement, and benefit from, the techniques of FIGS. 1 and 2.

In FIG. 13A, the smartphone 1302 is equipped with a first electrode 1304 and a second electrode 1306. In this example, both the electrodes 1304, 1306 are active electrodes, as both are in a default open circuit condition. The user 104 may utilize the touch pressure inputs described herein, for example, by holding the smartphone 1302 in a left hand and contacting the first electrode 1304 with the left hand, while pressing the second electrode 1306 with the right hand. Conversely, the same or different set of features may be obtained by holding the smartphone 1302 in a right hand and contacting the second electrode 1306 with the right hand, while pressing the first electrode 1304 with the left hand.

Although only the two electrodes 1304 and 1306 are illustrated in FIG. 13, positioned on sides of the smartphone 1302, it will be appreciated that more than two electrodes may be used, and may be positioned virtually anywhere on the smartphone 1302. Then, different combinations (e.g., pairs) may be used to implement different sets of user interaction features.

Figure 13B:
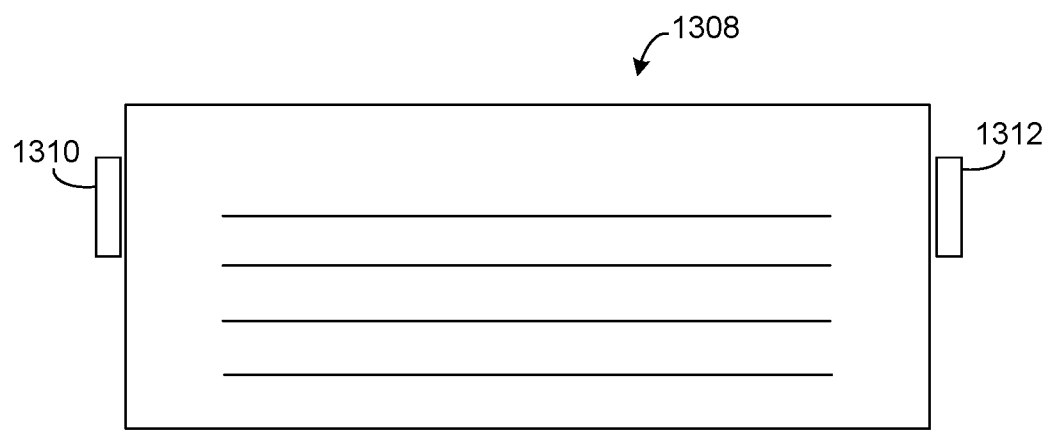
FIG. 13B is an example illustration of the system of FIG. 1, implemented using a keyboard.

FIG. 13B is an example illustration of the system of FIG. 1, implemented using a keyboard 1308. In FIG. 13B, the keyboard 1308 is equipped with a first electrode 1404 and a second electrode 1406. In this example, as in FIG. 13A, both the electrodes 1310, 1312 are active electrodes, as both are in a default open circuit condition. The user 104 may utilize the touch pressure inputs described herein, for example, by contacting the first electrode 1310 with the left hand, while pressing the second electrode 1312 with the right hand. Conversely, the same or different set of features may be obtained by contacting the second electrode 1312 with the right hand, while pressing the first electrode 1310 with the left hand.

As with the smartphone 1302 of FIG. 13A, more than two electrodes may be used with the keyboard 1308, and may be placed anywhere desired on the keyboard 1308. For example, electrodes may be applied at one or more keys of the keyboard 1308, so that pressure-dependent functions may be assigned to different pairs of keys. For example, a shift key or control key may be assigned as a first electrode, and then pressing any other key with another electrode would complete a key-specific circuit to perform a function with respect to that key. For example, different pressure levels could be assigned so that pressing a key with more pressure resulting in the corresponding letter being bolded, italicized, or underlined. In other implementations, shortcuts for various functions may be assigned to specific keys, and accessed by using assigned pressure levels. Thus, it will be appreciated that the techniques described herein for touch pressure input may be used in virtually any device, including peripheral devices, wearable devices, and combinations thereof.

Figure 14:
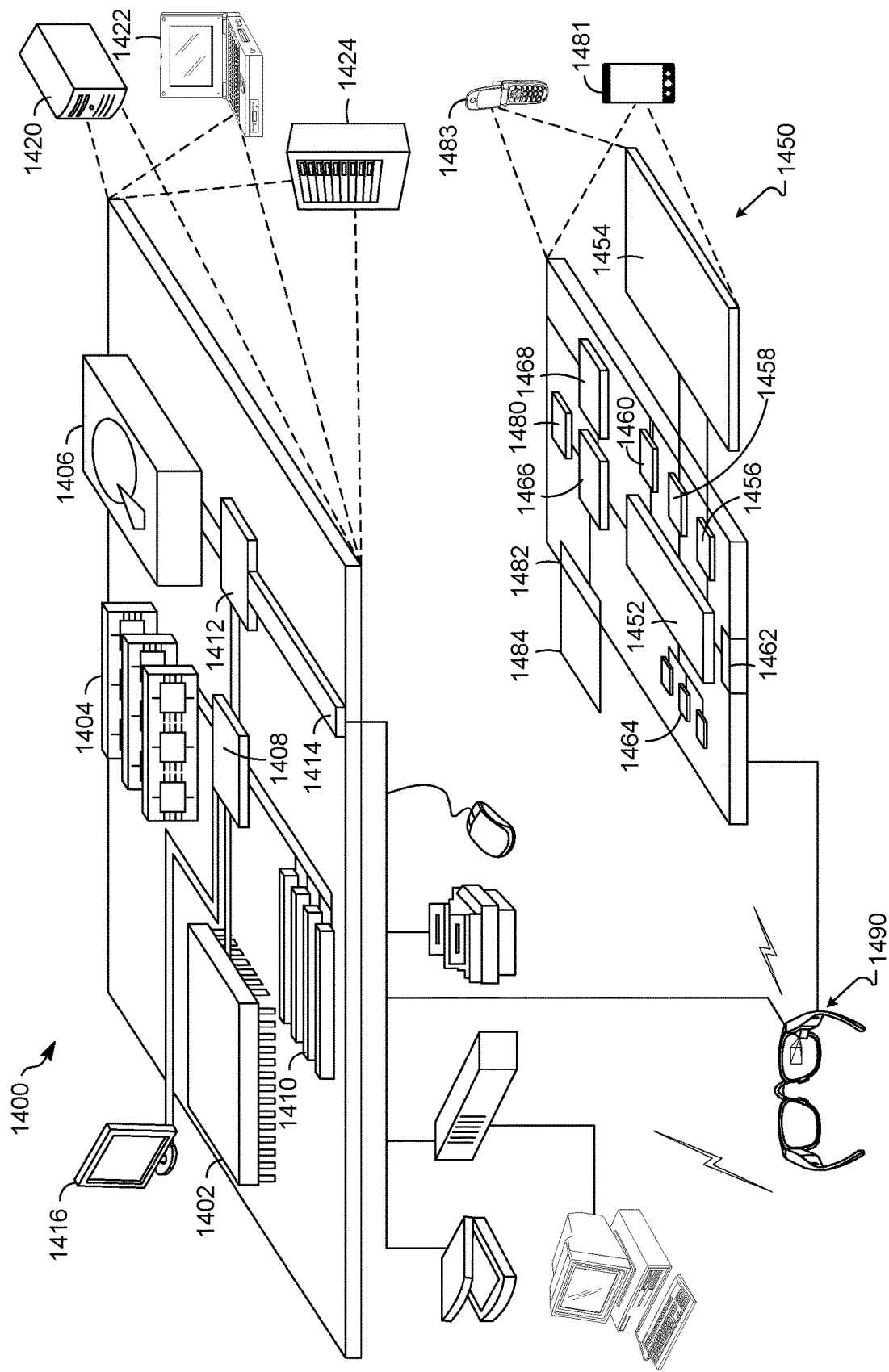
FIG. 14 shows an example of a computer device, mobile computer device and head mounted device according to at least one example implementation.

FIG. 14 shows an example of a computer device 1400 and a mobile computer device 1450, which may be used with the techniques described here. Computing device 1400 is intended to represent various forms of digital computers, such as laptops, desktops, tablets, workstations, personal digital assistants, smart devices, appliances, electronic sensor-based devices, televisions, servers, blade servers, mainframes, and other appropriate computing devices. Computing device 1450 is intended to represent various forms of mobile devices, such as personal digital assistants, cellular telephones, smart phones, and other similar computing devices. The components shown here, their connections and relationships, and their functions, are meant to be exemplary only, and are not meant to limit implementations described and/or claimed in this document.

Computing device 1400 includes a processor 1402, memory 1404, a storage device 1406, a high-speed interface 1408 connecting to memory 1404 and high-speed expansion ports 1410, and a low speed interface 1412 connecting to low speed bus 1414 and storage device 1406. The processor 1402 can be a semiconductor-based processor. The memory 1404 can be a semiconductor-based memory. Each of the components 1402, 1404, 1406, 1408, 1410, and 1412, are interconnected using various busses, and may be mounted on a common motherboard or in other manners as appropriate. The processor 1402 can process instructions for execution within the computing device 1400, including instructions stored in the memory 1404 or on the storage device 1406 to display graphical information for a GUI on an external input/output device, such as display 1416 coupled to high speed interface 1408. In other implementations, multiple processors and/or multiple buses may be used, as appropriate, along with multiple memories and types of memory. Also, multiple computing devices 1400 may be connected, with each device providing portions of the necessary operations (e.g., as a server bank, a group of blade servers, or a multi-processor system).

The memory 1404 stores information within the computing device 1400. In one implementation, the memory 1404 is a volatile memory unit or units. In another implementation, the memory 1404 is a non-volatile memory unit or units. The memory 1404 may also be another form of computer-readable medium, such as a magnetic or optical disk. In general, the computer-readable medium may be a non-transitory computer-readable medium.

The storage device 1406 is capable of providing mass storage for the computing device 1400. In one implementation, the storage device 1406 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods and/or computer-implemented methods, such as those described above. The information carrier is a computer- or machine-readable medium, such as the memory 1404, the storage device 1406, or memory on processor 1402.

The high speed controller 1408 manages bandwidth-intensive operations for the computing device 1400, while the low speed controller 1412 manages lower bandwidth-intensive operations. Such allocation of functions is exemplary only. In one implementation, the high-speed controller 1408 is coupled to memory 1404, display 1416 (e.g., through a graphics processor or accelerator), and to high-speed expansion ports 1410, which may accept various expansion cards (not shown). In the implementation, low-speed controller 1412 is coupled to storage device 1406 and low-speed expansion port 1414. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 1400 may be implemented in a number of different forms, as shown in the figure. For example, it may be implemented as a standard server 1420, or multiple times in a group of such servers. It may also be implemented as part of a rack server system 1424. In addition, it may be implemented in a computer such as a laptop computer 1422. Alternatively, components from computing device 1400 may be combined with other components in a mobile device (not shown), such as device 1450. Each of such devices may contain one or more of computing device 1400, 1450, and an entire system may be made up of multiple computing devices 1400, 1450 communicating with each other.

Computing device 1450 includes a processor 1452, memory 1464, an input/output device such as a display 1454, a communication interface 1466, and a transceiver 1468, among other components. The device 1450 may also be provided with a storage device, such as a microdrive or other device, to provide additional storage. Each of the components 1450, 1452, 1464, 1454, 1466, and 1468, are interconnected using various buses, and several of the components may be mounted on a common motherboard or in other manners as appropriate.

The processor 1452 can execute instructions within the computing device 1450, including instructions stored in the memory 1464. The processor may be implemented as a chipset of chips that include separate and multiple analog and digital processors. The processor may provide, for example, for coordination of the other components of the device 1450, such as control of user interfaces, applications run by device 1450, and wireless communication by device 1450.

Processor 1452 may communicate with a user through control interface 1458 and display interface 1456 coupled to a display 1454. The display 1454 may be, for example, a TFT LCD (Thin-Film-Transistor Liquid Crystal Display) or an OLED (Organic Light Emitting Diode) display, or other appropriate display technology. The display interface 1456 may comprise appropriate circuitry for driving the display 1454 to present graphical and other information to a user. The control interface 1458 may receive commands from a user and convert them for submission to the processor 1452. In addition, an external interface 1462 may be provided in communication with processor 1452, so as to enable near area communication of device 1450 with other devices. External interface 1462 may provide, for example, for wired communication in some implementations, or for wireless communication in other implementations, and multiple interfaces may also be used.

The memory 1464 stores information within the computing device 1450. The memory 1464 can be implemented as one or more of a computer-readable medium or media, a volatile memory unit or units, or a non-volatile memory unit or units. Expansion memory 1484 may also be provided and connected to device 1450 through expansion interface 1482, which may include, for example, a SIMM (Single In Line Memory Module) card interface. Such expansion memory 1484 may provide extra storage space for device 1450, or may also store applications or other information for device 1450. Specifically, expansion memory 1484 may include instructions to carry out or supplement the processes described above, and may include secure information also. Thus, for example, expansion memory 1484 may be provided as a security module for device 1450, and may be programmed with instructions that permit secure use of device 1450. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 1464, expansion memory 1484, or memory on processor 1452, that may be received, for example, over transceiver 1468 or external interface 1462.

Device 1450 may communicate wirelessly through communication interface 1466, which may include digital signal processing circuitry where necessary. Communication interface 1466 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 1468. In addition, short-range communication may occur, such as using a Bluetooth, low power Bluetooth, Wi-Fi, or other such transceiver (not shown). In addition, GPS (Global Positioning System) receiver module 1480 may provide additional navigation- and location-related wireless data to device 1450, which may be used as appropriate by applications running on device 1450.

Device 1450 may also communicate audibly using audio codec 1460, which may receive spoken information from a user and convert it to usable digital information. Audio codec 1460 may likewise generate audible sound for a user, such as through a speaker, e.g., in a handset of device 1450. Such sound may include sound from voice telephone calls, may include recorded sound (e.g., voice messages, music files, etc.) and may also include sound generated by applications operating on device 1450.

The computing device 1450 may be implemented in a number of different forms, as shown in the figure. For example, it may be implemented as a cellular telephone 1483. It may also be implemented as part of a smart phone 1481, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as modules, programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor, or LED (light emitting diode)) for displaying information to the user and a keyboard and a pointing device (e.g., a mouse or a trackball) by which the user can provide input to the computer. Other kinds of devices can be used to provide for interaction with a user as well. For example, feedback provided to the user can be any form of sensory feedback (e.g., visual feedback, auditory feedback, or tactile feedback), and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

In some implementations, the computing devices depicted in FIG. 14 can include sensors that interface with, or are included in, a HMD 1490. For example, one or more sensors included on computing device 1450 or other computing device depicted in FIG. 14, can provide input to HMD 1490 or in general, provide input to that can be used by the HMD 1490. The sensors can include, but are not limited to, a touchscreen, accelerometers, gyroscopes, pressure sensors, biometric sensors, temperature sensors, humidity sensors, and ambient light sensors. Computing device 1450 (e.g., the HMD 1490) can use the sensors to determine an absolute position and/or a detected rotation of the HMD 1490 that can then be used as input for use by the HMD 1490.

In some implementations, one or more input devices included on, or connected to, the computing device 1450 and/or the HMD 1490 can be used as inputs for use by the HMD 1490. The input devices can include, but are not limited to, a touchscreen, a keyboard, one or more buttons, a trackpad, a touchpad, a pointing device, a mouse, a trackball, a joystick, a camera, a microphone, earphones or buds with input functionality, a gaming controller, or other connectable input device.

In some implementations, one or more output devices included on the computing device 1450, and/or in the HMD 1490, can provide output and/or feedback to a user of the HMD 1490. The output and feedback can be visual, tactical, or audio. The output and/or feedback can include, but is not limited to, rendering a display of the HMD 1490, vibrations, turning on and off or blinking and/or flashing of one or more lights or strobes, sounding an alarm, playing a chime, playing a song, and playing of an audio file. The output devices can include, but are not limited to, vibration motors, vibration coils, piezoelectric devices, electrostatic devices, light emitting diodes (LEDs), strobes, and speakers.

In some implementations, computing device 1450 can be placed within HMD 1490 to create an integrated HMD system. HMD 1490 can include one or more positioning elements that allow for the placement of computing device 1450, such as smart phone 1481, in the appropriate position within HMD 1490. In such implementations, the display of smart phone 1481 can render images using a display of the HMD 1490.

In some implementations, the computing device 1450 may appear as another object in a computer-generated, 3D environment. Interactions by the user with the computing device 1450 (e.g., rotating, shaking, touching a touchscreen, swiping a finger across a touch screen) can be interpreted as interactions with the object in the AR/VR space. As just one example, computing device can be a laser pointer. In such an example, computing device 1450 appears as a virtual laser pointer in the computer-generated, 3D environment. As the user manipulates computing device 1450, the user in the AR/VR space sees movement of the laser pointer. The user receives feedback from interactions with the computing device 1450 in the AR/VR environment on the computing device 1450 or on the HMD 1490.

In some implementations, a computing device 1450 may include a touchscreen. For example, a user can interact with the touchscreen in a particular manner that can mimic what happens on the touchscreen with what happens in a display of the HMD 1490. For example, a user may use a pinching-type motion to zoom content displayed on the touchscreen. This pinching-type motion on the touchscreen can cause information provided in display to be zoomed. In another example, the computing device may be rendered as a virtual book in a computer-generated, 3D environment.

In some implementations, one or more input devices in addition to the computing device (e.g., a mouse, a keyboard) can be rendered in a display of the HMD 1490. The rendered input devices (e.g., the rendered mouse, the rendered keyboard) can be used as rendered in the in the display.

A number of implementations have been described. Nevertheless, it will be understood that various modifications may be made without departing from the spirit and scope of the description and claims.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other implementations are within the scope of the following claims.

Further to the descriptions above, a user is provided with controls allowing the user to make an election as to both if and when systems, programs, devices, networks, or features described herein may enable collection of user information (e.g., information about a user's social network, social actions, or activities, profession, a user's preferences, or a user's current location), and if the user is sent content or communications from a server. In addition, certain data may be treated in one or more ways before it is stored or used, so that user information is removed. For example, a user's identity may be treated so that no user information can be determined for the user, or a user's geographic location may be generalized where location information is obtained (such as to a city, ZIP code, or state level), so that a particular location of a user cannot be determined. Thus, the user may have control over what information is collected about the user, how that information is used, and what information is provided to the user.

The computer system (e.g., computing device) may be configured to wirelessly communicate with a network server over a network via a communication link established with the network server using any known wireless communications technologies and protocols including radio frequency (RF), microwave frequency (MWF), and/or infrared frequency (IRF) wireless communications technologies and protocols adapted for communication over the network.

In accordance with aspects of the disclosure, implementations of various techniques described herein may be implemented in digital electronic circuitry, or in computer hardware, firmware, software, or in combinations of them. Implementations may be implemented as a computer program product (e.g., a computer program tangibly embodied in an information carrier, a machine-readable storage device, a computer-readable medium, a tangible computer-readable medium), for processing by, or to control the operation of, data processing apparatus (e.g., a programmable processor, a computer, or multiple computers). In some implementations, a tangible computer-readable storage medium may be configured to store instructions that when executed cause a processor to perform a process. A computer program, such as the computer program(s) described above, may be written in any form of programming language, including compiled or interpreted languages, and may be deployed in any form, including as a standalone program or as a module, component, subroutine, or other unit suitable for use in a computing environment. A computer program may be deployed to be processed on one computer or on multiple computers at one site or distributed across multiple sites and interconnected by a communication network.

Specific structural and functional details disclosed herein are merely representative for purposes of describing example implementations. Example implementations, however, may be embodied in many alternate forms and should not be construed as limited to only the implementations set forth herein.

The terminology used herein is for the purpose of describing particular implementations only and is not intended to be limiting of the implementations. As used herein, the singular forms "a," "an," and "the" are intended to include the plural forms as well, unless the context clearly indicates otherwise. It will be further understood that the terms "comprises," "comprising," "includes," and/or "including," when used in this specification, specify the presence of the stated features, steps, operations, elements, and/or components, but do not preclude the presence or addition of one or more other features, steps, operations, elements, components, and/or groups thereof.

It will be understood that when an element is referred to as being "coupled," "connected," or "responsive" to, or "on," another element, it can be directly coupled, connected, or responsive to, or on, the other element, or intervening elements may also be present. In contrast, when an element is referred to as being "directly coupled," "directly connected," or "directly responsive" to, or "directly on," another element, there are no intervening elements present. As used herein the term "and/or" includes any and all combinations of one or more of the associated listed items.

Spatially relative terms, such as "beneath," "below," "lower," "above," "upper," and the like, may be used herein for ease of description to describe one element or feature in relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" can encompass both an orientation of above and below. The device may be otherwise oriented (rotated 130 degrees or at other orientations) and the spatially relative descriptors used herein may be interpreted accordingly.

Example implementations of the concepts are described herein with reference to cross-sectional illustrations that are schematic illustrations of idealized implementations (and intermediate structures) of example implementations. As such, variations from the shapes of the illustrations as a result, for example, of manufacturing techniques and/or tolerances, are to be expected. Thus, example implementations of the described concepts should not be construed as limited to the particular shapes of regions illustrated herein but are to include deviations in shapes that result, for example, from manufacturing. Accordingly, the regions illustrated in the figures are schematic in nature and their shapes are not intended to illustrate the actual shape of a region of a device and are not intended to limit the scope of example implementations.

It will be understood that although the terms "first," "second," etc. may be used herein to describe various elements, these elements should not be limited by these terms. These terms are only used to distinguish one element from another. Thus, a "first" element could be termed a "second" element without departing from the teachings of the present implementations.

Unless otherwise defined, the terms (including technical and scientific terms) used herein have the same meaning as commonly understood by one of ordinary skill in the art to which these concepts belong. It will be further understood that terms, such as those defined in commonly used dictionaries, should be interpreted as having a meaning that is consistent with their meaning in the context of the relevant art and/or the present specification and will not be interpreted in an idealized or overly formal sense unless expressly so defined herein.

While certain features of the described implementations have been illustrated as described herein, many modifications, substitutions, changes, and equivalents will now occur to those skilled in the art. It is, therefore, to be understood that the appended claims are intended to cover such modifications and changes as fall within the scope of the implementations. It should be understood that they have been presented by way of example only, not limitation, and various changes in form and details may be made. Any portion of the apparatus and/or methods described herein may be combined in any combination, except mutually exclusive combinations. The implementations described herein can include various combinations and/or sub-combinations of the functions, components, and/or features of the different implementations described.

What is claimed is:

1. A computing device comprising:
    a processor;
    a storage medium storing instructions;
    a body; and
    at least two electrodes mounted on the body and in contact with a user of the computing device,
    wherein the instructions, when executed by the processor, cause the computing device to
        determine an electrical signal associated with a circuit that includes the at least two electrodes and the user, the electrical signal including an electrocardiography (ECG) signal characterizing electrical activities of a heart of the user;
        filter the ECG signal to obtain a filtered signal in which components related to the electrical activities of the heart of the user have been removed;
        determine, from the filtered signal, a pressure applied to at least one electrode of the at least two electrodes; and implement at least one function of the computing device, based on the pressure.

2. The computing device of claim 1, further configured to:
determine, from the filtered signal, motion artifacts corresponding to the pressure applied by the user to the at least one electrode; and
determine the pressure, based on the motion artifacts.

3. The computing device of claim 1, wherein the at least two electrodes include a passive electrode in default contact with the user during use of the at least one computing device, and the at least one electrode includes an active electrode that receives a press from the user to implement the at least one function.

4. The computing device of claim 1, further configured to:
determine the pressure as having at least one pressure level from among a plurality of pre-defined pressure levels, based on the electrical signal and at least one pre-determined relationship between electrical signals and the pre-defined pressure levels.

5. The computing device of claim 4, wherein the at least one pre-determined relationship includes a heuristic model.

6. The computing device of claim 1, further configured to:
access a machine learning model trained to classify electrical signal artifacts as corresponding pressure levels; and
determine the pressure from among the pressure levels, using the machine learning model.

7. The computing device of claim 1, further configured to:
determine the pressure as having a pressure level from among a plurality of pre-defined pressure levels; and
implement the at least one function including selecting or operating the at least one function in response to the pressure level.

8. The computing device of claim 1, further configured to:
determine the pressure as having a pressure level from among a plurality of pre-defined pressure levels; and
generate a feedback signal indicating the pressure level.

9. The computing device of claim 1, wherein the computing device includes at least one wearable device, and the at least two electrodes include a passive electrode that is in default contact with a skin surface of the user while the at least one wearable device is being worn, and the at least one electrode includes an active electrode that is accessible to the user to receive the pressure applied thereto by the user.

10. The computing device of claim 1, wherein the at least two electrodes include at least three electrodes, the computing device further configured to:
determine a second electrical signal at the computing device, the second electrical signal associated with a second circuit that includes a different electrode combination of the at least three electrodes than the circuit;
determine, from the second electrical signal, a second pressure applied to at least one electrode of the different electrode combination; and
implement at least a second function of the computing device, based on the second pressure.

11. A computer-implemented method for operating a computing device having a processor, a storage medium storing instructions executable by the processor to perform the computer-implemented method, and a body with at least two electrodes mounted thereon, the method comprising:
determining an electrical signal at the computing device, the electrical signal associated with a circuit that includes the at least two electrodes in contact with a user of the computing device, and the user, the electrical signal including an electrocardiography (ECG) signal characterizing electrical activities of a heart of the user;
filter the ECG signal to obtain a filtered signal in which components related to the electrical activities of the heart of the user have been removed;
determining, from the filtered signal, a pressure applied to at least one electrode of the at least two electrodes; and
implementing at least one function of the computing device, based on the pressure.

12. The method of claim 2, further comprising:
determining, from the filtered signal, motion artifacts corresponding to motions of the user in applying the pressure to the at least one electrode; and
determining the pressure, based on the motion artifacts.

13. The method of claim 11, further comprising:
determining the pressure as having at least one pressure level from among a plurality of pre-defined pressure levels, based on the electrical signal and at least one pre-determined relationship between electrical signals and the pre-defined pressure levels.

14. The method of claim 13, wherein the at least one pre-determined relationship includes a heuristic model.

15. The method of claim 11, further comprising:
determining the pressure as having a pressure level from among a plurality of pre-defined pressure levels; and
implementing the at least one function including selecting or operating the at least one function in response to the pressure level.

16. A computer program product, the computer program product being tangibly embodied on a non-transitory computer-readable storage medium and comprising instructions that, when executed by a computing device, are configured to cause the computing device to
determine an electrical signal at the computing device, the electrical signal associated with a circuit that includes at least two electrodes mounted on a body of the computing device and in contact with a user of the computing device, and the user, the electrical signal including an electrocardiography (ECG) signal characterizing electrical activities of a heart of the user;
filter the ECG signal to obtain a filtered signal in which components related to the electrical activities of the heart of the user have been removed;
determine, from the filtered signal, a pressure applied to at least one electrode of the at least two electrodes; and
implement at least one function of the computing device, based on the pressure.

17. The computer program product of claim 16, wherein the instructions, when executed, are further configured to cause the computing device to:
determine, from the filtered signal, motion artifacts corresponding to motions of the user in applying the pressure to the at least one electrode; and
determine the pressure, based on the motion artifacts.

18. The computer program product of claim 16, wherein the instructions, when executed, are further configured to cause the computing device to:
determine the pressure as having a pressure level from among a plurality of pre-defined pressure levels; and
generate a feedback signal indicating the pressure level.

* * * * *